United States Patent [19]

Koyama

[11] Patent Number: 4,618,979
[45] Date of Patent: Oct. 21, 1986

[54] X-RAY FLUOROSCOPIC/RADIOGRAPHIC APPARATUS

[75] Inventor: Katsuhide Koyama, Yaita, Japan

[73] Assignee: Kabushiki Kaisha Toshiba, Japan

[21] Appl. No.: 616,151

[22] Filed: Jun. 1, 1984

[30] Foreign Application Priority Data

Jun. 3, 1983 [JP] Japan .................................. 58-99151

[51] Int. Cl.⁴ .............................................. G03B 42/02
[52] U.S. Cl. ...................................... 378/176; 378/181
[58] Field of Search ................. 378/175, 176, 167, 181

[56] References Cited

U.S. PATENT DOCUMENTS 4,105,920  8/1978  Pury et al. ........................... 378/176
4,432,095  2/1984  Adelmeyer et al. ................. 378/176

Primary Examiner—Carolyn E. Fields
Attorney, Agent, or Firm—Finnegan, Henderson, Farabow, Garrett & Dunner

[57] ABSTRACT

A main carriage has four wheels each of which is supported by a corresponding guide rail. The main carriage is reciprocated between a standby position and a photographing position along the guide rails through the wheels. The wheels engaged with the guide rails at the two sides of the apparatus housing are rotatably mounted at the main carriage. The wheel engaged with the edge of the main carriage at the side of a film convey mechanism is mounted on the main carriage to be movable along its moving direction (X direction). A guide plate is fixed on a main body of the main carriage, and a guide hole is formed in the guide rail to extend along the X direction. A pair of supports are engaged in the guide hole, and a support plate is fixed to the supports. A wheel is rotatably mounted on an end of the support plate. The support plate is biased by a tension spring in the retracting direction of the main carriage. When the main carriage is at the standby position, the support plate is moved in the advancing direction of the main carriage relative thereto since the wheel is stopped by a stopper. When the main carriage is at the photographing position, the support plate is projected in the retracting direction of the main carriage by the spring. The length of the guide rail can be shortened by a length corresponding to the moving distance of the support plate.

8 Claims, 7 Drawing Figures

X-RAY FLUOROSCOPIC/RADIOGRAPHIC APPARATUS

BACKGROUND OF THE INVENTION

The present invention relates to an X-ray fluoroscopic/radiographic apparatus and, more particularly, to an improvement in a moving mechanism for moving a main carriage carrying an X-ray spot shot film for X-ray radiography thereon between the standby position and the photographing position in an X-ray fluoroscopic/radiographic apparatus having both functions of X-ray fluoroscopy utilizing an X-ray image detector such as an X-ray image intensifier (hereinafter abbreviated as I.I.) and of X-ray radiography utilizing X-ray film.

In an X-ray fluoroscopic/radiographic apparatus, an X-ray fluoroscopic image detected by an I.I. is monitored on a TV screen to perform fluoroscopic diagnosis. Then, X-ray radiography of the desired portion of the body of a patient is performed with an X-ray spot shot apparatus.

FIG. 1 shows a plan view of a moving mechanism of a main carriage 10 in the X-ray spot shot apparatus, and FIG. 2 shows a partial longitudinal sectional view thereof. Wheels 12, 14, 16 and 18 are axially supported to be rotatable at four positions of the main carriage 10. The wheels 12 and 14 are supported by a guide rail 20, the wheel 16 is supported by a guide rail 22, and the wheel 18 is supported by a guide rail 24. Referring to FIG. 1, the main carriage 10 is reciprocal along the directions indicated by the arrows X on the guide rail 20, 22 and 24 by a distance L between the standby position (hereinafter abbreviated as the F position) indicated by the solid line and the photographing position (hereinafter abbreviated as the R position) indicated by the broken line. A film supply and store device is arranged beneath the main carriage 10 at the F position. More specifically, a film magazine is arranged underneath the main carriage 10. A film drawn by suction from a suction cup is moved upward by a convey mechanism and is fed to an inner carriage (not shown) on the main carriage 10 from the side of the wheels 16 and 18 along the direction indicated by arrow Y. Rollers or the like of the film convey mechanism are arranged near that portion of the main carriage 10 at the side of the wheel 18. An I.I. 26 is arranged above the main carriage 10 at the R position. The I.I. 26 is formed integrally with a cover 30 covering an opening formed in the housing of the apparatus so as to allow an I.I. 28 having a large diameter to be set thereon. An X-ray source (not shown) is arranged below the I.I. 28 with the main carriage 10 interposed therebetween. The film conveyed and held in the inner carriage on the main carriage by the film convey mechanism is moved into the R position, and X-ray radiography is performed when the main carriage 10 is advanced in the direction indicated by the arrow X. Then, the main carriage 10 is retracted to the F position in the X direction. After photography, the film is transferred to the film convey mechanism at this F position and is stored in the film store magazine.

Recently, a great demand for a more compact and lightweight X-ray fluoroscopic/radiographic apparatus has arisen. In consideration of this demand, the length of the main carriage 10 along the advancing/retracting direction (X direction) is determined to have a mimimum value which is, in turn, determined in accordance with the size of the film. In this case, since the rail 22 for the front right wheel 16 of the main carriage 10 is disposed outwardly from the rail 24, it does not interfere with the I.I.'s ability to detect X-rays. However, the distal end of the rail 24 disposed inwardly from the rail 22 is very close to the input field from view of the I.I. 28. In this case, when an I.I. 28 having a large input diameter is mounted for achieving a highly accurate diagnosis, the distal end of the guide rail 24 extends into the input field of view of the I.I. 28 by a distance T, thus interfering with correct X-ray diagnosis. However, if the guide rail 24 is located at an outward position or the length of the main carriage 10 along the X direction is elongated to place the wheel 18 at a rearward position, the overall apparatus becomes bulky.

SUMMARY OF THE INVENTION

It is an object of the present invention to provide an X-ray fluoroscopic/radiographic apparatus which is compact in size, and light in weight and which allows the use of an X-ray image detector such as an I.I. having a wide input field of view.

An X-ray fluoroscopic/radiographic apparatus for photographing an X-ray image on a film according to the present invention, comprises:

a carriage for conveying the film between a standby position for receiving or supplying the film, and a photographing position for photographing the X-ray image on the film;

a plurality of guide rails which extend parallel to each other along X directions connecting the standby and photographing positions of the carriage;

a plurality of wheels which is mounted on the carriage and which is movable along each of the plurality of guide rails upon engagement thereon; and a support mechanism which is mounted on the carriage and which supports at least one wheel to be movable relative to the carriage by a predetermined distance S along the X directions, the wheel supported by the support mechanism being moved by a distance shorter than the moving distance of the carriage by the distance S along the corresponding guide rail.

According to the present invention, the wheel supported by the guide rail near the X-ray image detector such as an I.I. can be moved relative to the carriage by the distance S along the advancing/retracting direction of the carriage. Therefore, even if the carriage is moved by a distance L from the standby position to the photographing position, the wheel supported by the support mechanism is moved only by a distance (L−S) relative to the apparatus housing. As a consequence, the length of the guide rail engaged with this wheel can be shortened by a length corresponding to the distance S, as compared to the conventional case wherein such a support mechanism as described above is not used. Therefore, even if an I.I. having a large diameter is mounted, the guide rail will not interfere with the input field of view of the I.I. Along with this, the overall apparatus can be rendered compact in size and light in weight. In this manner, the present invention provides an X-ray fluoroscopic/radiographic apparatus which has a simple construction, which is compact in size and light in weight, and which allows the use of many types of I.Is.

DETAILED DESCRIPTION OF THE PREFERRED EMBODIMENTS

Figure 1:
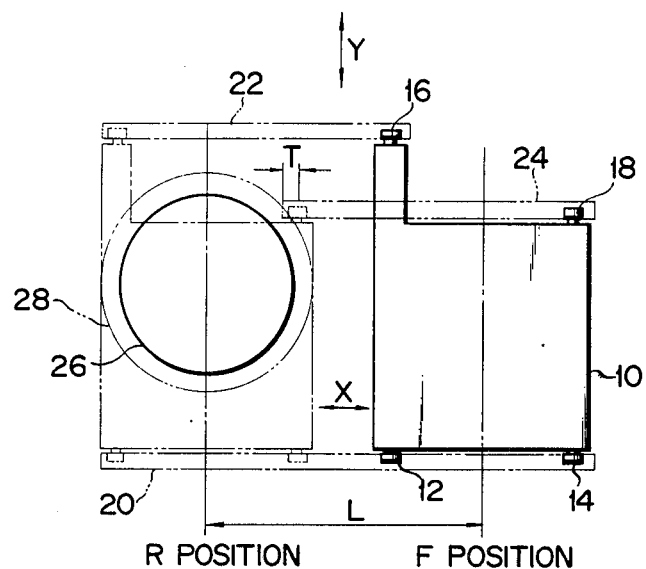
FIG. 1 is a plan view of a moving mechanism of a main carriage of a conventional X-ray fluoroscopic/radiographic apparatus.
Figure 2:
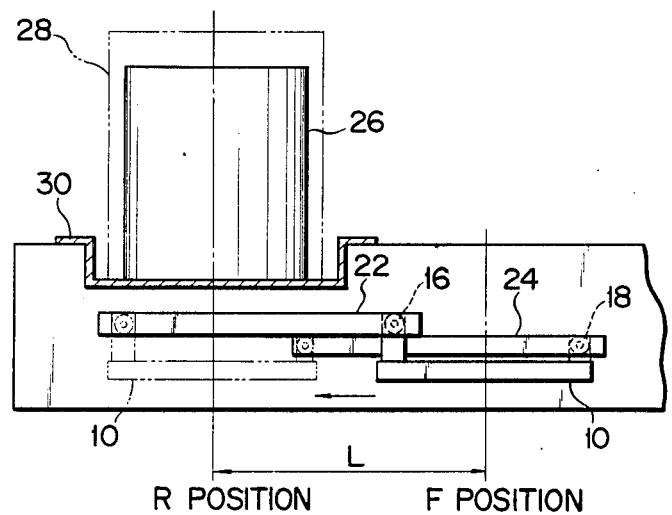
FIG. 2 is a partial longitudinal sectional view of the apparatus shown in FIG. 1.
Figure 3:
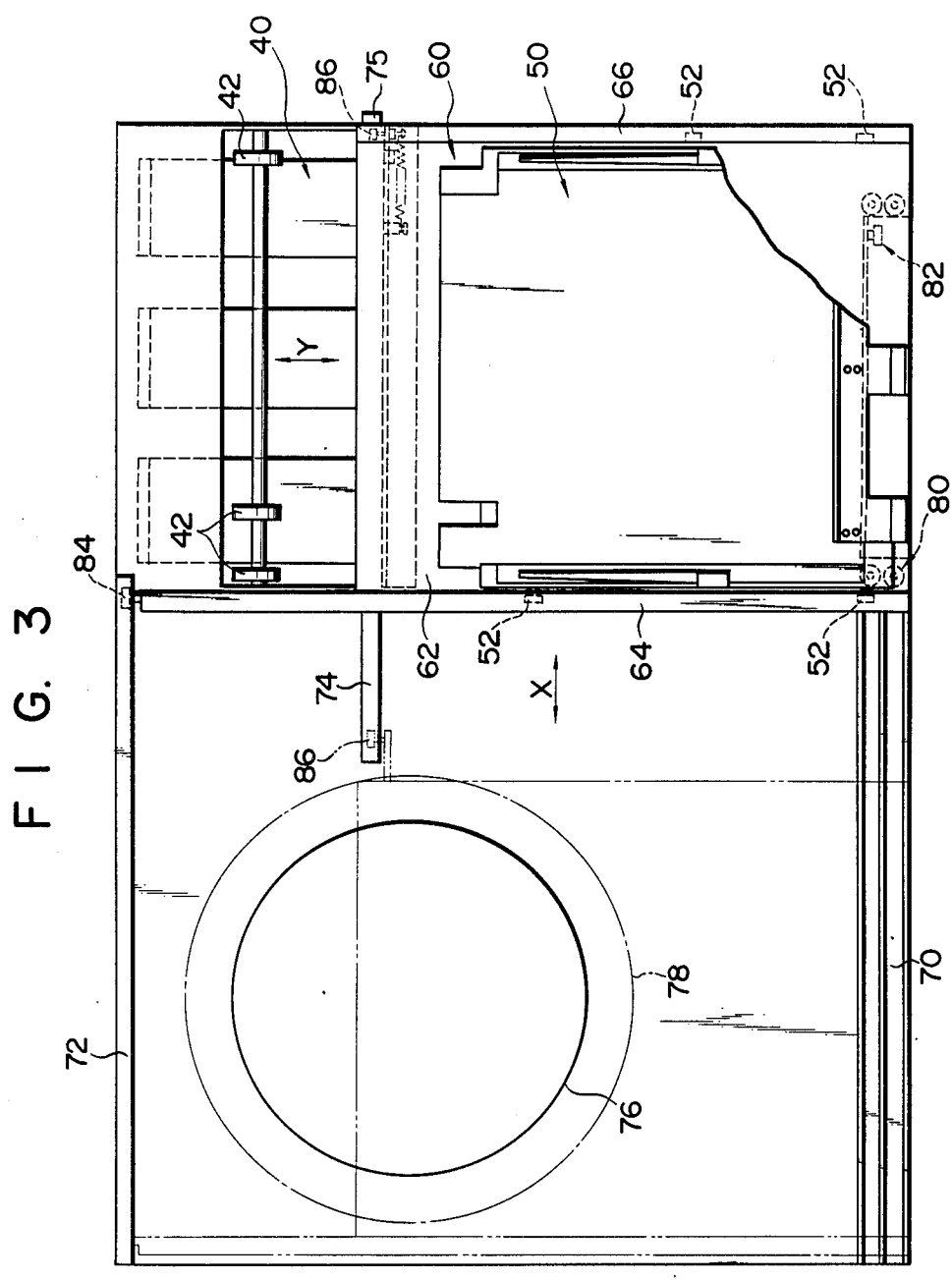
FIG. 3 is a plan view of an X-ray fluoroscopic/radiographic apparatus according to one embodiment of the present invention.
Figure 4:
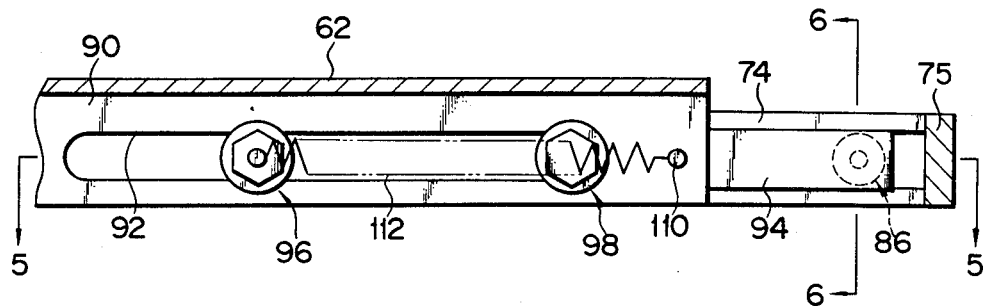
FIG. 4 is an enlarged, longitudinal sectional view of the apparatus shown in FIG. 3.
Figure 5:
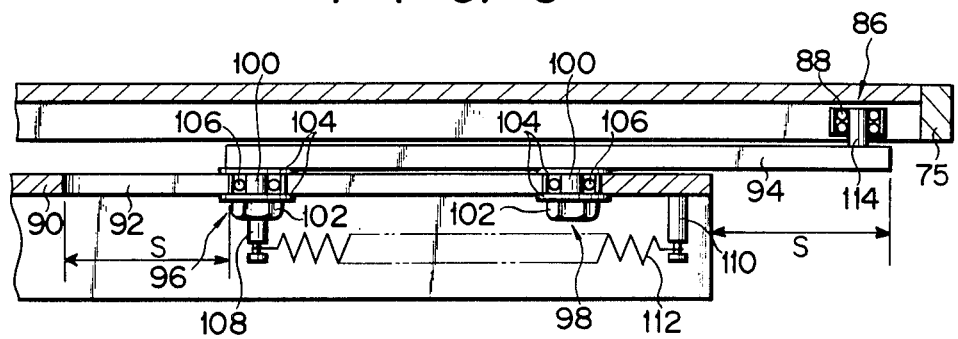
FIG. 5 is a sectional view along the line 5—5 of FIG. 4.
Figure 6:
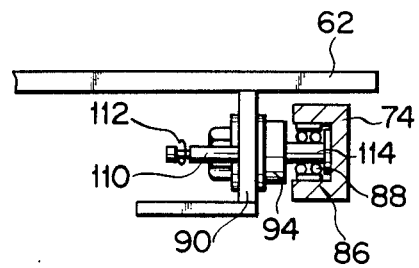
FIG. 6 is a sectional view along the line 6—6 of FIG. 4.

FIG. 3 is a plan view of an X-ray fluoroscopic/radiographic apparatus according to an embodiment of the present invention; FIG. 4 is an enlarged, longitudinal sectional view of the apparatus shown in FIG. 3; FIG. 5 is a sectional view along the line 5—5 of FIG. 4; and FIG. 6 is a sectional view along the line 6—6 of FIG. 4. Referring to FIG. 3, a main carriage 60 is at the standby position (F position) indicated by the solid line. A film convey mechanism 40 is arranged underneath the main carriage 60. A film drawn by suction by a suction cup from a film supply magazine (not shown) arranged inside the apparatus housing is conveyed to a upper position of the housing. The outlet port of the convey mechanism 40 is substantially level with the main carriage 60. The film is conveyed in the Y direction toward an inner carriage 50 in the main carriage 60 by rollers 42 at the outlet port of the convey mechanism 40.

The main carriage 60 has a main body 62, and a pair of guide rails 64 and 66 which extend along the Y direction and which are arranged at those side edges of the main body 62 which are opposite to each other along the X direction. The guide rail 64 extends along the entire length of the housing in the Y direction. On the other hand, the guide rail 66 extends only to a position in front of the convey mechanism 40. The main body 62 has a length corresponding to the length of the guide rail 66 in the Y direction. Therefore, the guide rail 64 projects from the main body 62 by a distance corresponding to the difference between the lengths of the guide rails 64 and 66.

An inner carriage 50 has two pairs of wheels 52 at those side edges thereof which oppose each other along the X direction. Each wheel 52 has a bearing structure and is supported by the guide rails 64 and 66. The inner carriage 50 is reciprocated along the Y directions on the guide rails 64 and 66 through the wheels 52. The inner carriage 50 is advanced toward the rollers 42, receives the film near the rollers 42, and clamps the film between upper and lower plates of the inner carriage 50 which are of a material which can transmit X-rays. The inner carriage 50 clamping the film is retracted along the guide rails 64 and 66.

Guide rails 70 and 72 are arranged at those side edges of the housing which oppose each other along the Y direction. The guide rail 70 extends along the entire length of the housing along the X direction. On the other hand, the guide rail 72 extends only to a position in front of the convey mechanism 40. A guide rail 74 extends along the X direction from that side edge of the main carriage 60 which is at the side of the convey mechanism 40 of the main body 62 of the main carriage 60. An I.I. 76 is mounted in the portion of the interior of the housing in which the convey mechanism 40 is not arranged. An I.I. 78 of a large diameter can be mounted in place of the standard I.I. 76. The guide rail 74 extends to a position in front of the input field of view of the I.I. 78.

A guided member or wheel 84 engaging with the guide rail 72 is rotatably mounted at that end of the guide rail 64 of the main carriage 60 which is at the side of the guide rail 72. Drive and guide wheel units 80 and 82 are arranged at that end of the main body 62 which is at the side of the guide rail 70. Each of the wheel units 80 and 82 has a pair of guided members or wheels which regulate the horizontal position of the main body 62 and another wheel for regulating the vertical position thereof. The main carriage 60 also has a guided member or wheel 86 which engages with the guide rail 74 and which is arranged at that end of the guide rail 66 which is at the side of the guide rail 74. Each wheel has a bearing structure and can move along the guide rails. Thus, the main carriage 60 can reciprocate along the guide rails 70, 72 and 74 in the X directions. An X-ray source (not shown) such as an X-ray tube is arranged immediately above the center of photographing field of the I.I. 76. When the inner carriage 50 receives the film, the main carriage 60 is advanced in the X direction and is stopped at the photographing position (R position). When only a quarter of the film is to be used for photography, the inner carriage 50 is moved along the guide rails 64 and 66 so as to control the position of the film.

The mechanism for supporting the wheel 86 on the main body 62 will now be described. As shown in FIGS. 4 to 6, a guide plate 90 is fixed to the lower surface of the main body 62 so as to extend parallel to the guide rail 74 and at a right angle to the main body 62. An elongated guide hole 92 extends along the X direction and is formed at that end of the guide plate 90 which is at the side of the guide rail 66. A pair of supports 96 and 98 are arranged in the guide hole 92 such that they are separated along the direction of elongation thereof. Each support 96 or 98 has a shaft 100 crossing the guide hole 92, a bearing 106 fitted around the shaft 100 and fitted in the guide hole 92, and a pair of support pieces 104 fitted around the shaft 100. A support plate 94 is fixed to the shafts 100 of the supports 96 and 98. The support pieces 104 and the bearings 106 are fixed on the shafts 100 such that nuts 102 and the support pieces 104 tightly sandwich the guide plate 90 therebetween and the bearings 106 engage with the guide hole 92. A stopper 108 is mounted on the shaft 100 of the support 96. A stopper 110 is fixed to the position of the guide plate 90 at which it opposes the stopper 108 along the X direction. A tension spring 112 is mounted between the stoppers 108 and 110. When the supports 96 and 98 move within the guide hole 92, the support plate 94 can reciprocate by a predetermined distance S along the X direction. The support plate 94 is normally biased by the spring 112 in the retracting direction of the main carriage 60. Therefore, when no external force is acting on the support plate 94, the support plate 94 is in the state shown in the figure, i.e., a state wherein the support 98 abuts against that end of the guide hole 92 which is at the side of the stopper 110. In this state, the support plate 94 projects from the main body 62 or the guide plate 90 by the predetermined distance S. The wheel 86 is arranged at the projecting end of the support plate 94. The wheel 86 has a shaft 114 fixed to the support plate 94, and a bearing 88 fitted outside the shaft 114 and engaged with the guide rail 74. The wheel 86 can move along the guide rail 74 by means of the bearing 88. A stopper 75 is fixed at that end of the guide rail 74 which is at the side of the guide rail 66. When the wheel 86 contacts the stopper 76 and the main carriage 60 is retracted, the support plate 94 is moved relative to the guide plate 90 until the support 96 abuts against the end of the guide hole 92.

The operation of the apparatus having the above construction will now be described. The main carriage 60 is supported by the guide rails 70, 72 and 74 through the wheels 80, 82, 84 and 86. The main carriage 60 at the F position receives the film from the convey mechanism 40. The main carriage 60 is advanced on the guide rails 70, 72 and 74 in the X direction and is stopped at the R position. When the main carriage 60 reaches the R position, the film is exposed to X-rays. The main carriage 60 is then retracted in the X direction and is stopped at the F position. The inner carriage 50 is advanced in the Y direction, and the exposed film is supplied to the convey mechanism 40. In this case, the wheels 80, 82 and 84 are moved from the F position to the R position by the distance L. However, the wheel 86 is moved by the distance (L−S) which is shorter than the distance L by the distance S. Thus, when the main carriage 60 is at the F position, the wheel 86 contacts the stopper 75, and the edge of the support plate 94 is level with that of the main body 62. When the main carriage 60 is advanced in the X direction, the support plate 94 projects from the main body 62 by the distance S. When the wheel 86 is separated from the stopper 75, the support plate 94 projects from the main body 62 by the distance S. Therefore, the distance of displacement of the wheel 86 relative to the main body 62 becomes (L−S). For this reason, the length of the guide rail 74 can be (L−S) so that the length of the guide rail can be shorter than that of a conventional apparatus by a length corresponding to the distance S. In other words, the side edge of the guide rail 74 at the side of the I.I. 76 can be located rearward by the distance S. Even if an I.I. 78 of a large input diameter is mounted, the guide rail 74 will not interfere with the input field of view of the I.I. 78. The size of the overall apparatus can thus be reduced to the minimum size which is determined by the size of the main carriage or the like, so that a compact and lightweight apparatus can be obtained.

Figure 7:
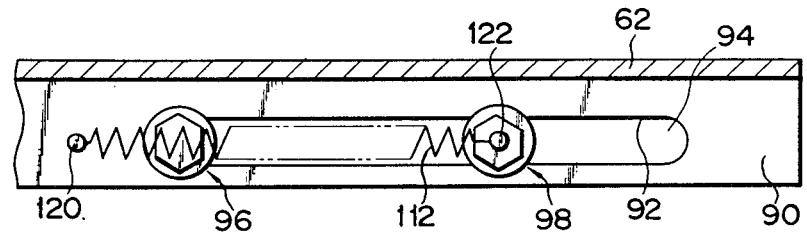
FIG. 7 is a partial sectional view showing another embodiment of the present invention.

FIG. 7 shows another embodiment of the present invention. The same reference numerals as in FIGS. 3 to 6 denote the same parts in FIG. 7. A stopper 122 is fixed to the support 98 in place of the stopper 108. A stopper 120 is fixed to that portion of the guide plate 90 which is closer to the guide rail 64 than the support 98 is. A tension spring 112 is mounted between the stoppers 120 and 122. Thus, the support plate 94 is biased toward the guide rail 64 by the spring 112. In this embodiment, the stopper 75 of the guide rail 74 is arranged at that end of the guide rail 74 which is at the side of the I.I. 76.

In this embodiment, when the main carriage 60 is advanced in the X direction, the wheel 86 is abutted against the stopper 75 and the support plate 94 is moved relative to the main body 62 toward the guide rail 66. That is, since the support plate 94 projects from the main carriage 60 by the distance S, the length of the guide rail 74 can also be reduced by a length corresponding to the distance S.

The present invention is not limited to the particular embodiments described above, and various other changes and modifications can be made within the spirit and scope of the present invention. For example, the support plate 94 need not be biased in one direction by the spring 112. No problem is encountered even if the spring 112 is omitted. When the main carriage is at the F position in FIG. 4 or in the R position in FIG. 7, the edge of the support plate 94 need not correspond to that of the guide plate 90. The length of the guide rail 74 can be further decreased if the length of the guide hole 92 is increased.

What is claimed is:

1. An X-ray fluoroscopic/radiographic apparatus for photographing an X-ray image on a film, comprising:
   carriage means movable along an X axis for conveying the film between a standby position, where said carriage means receives and supplies the film, and a photographing position, where the X-ray image is photographed on the film, said standby and photographing positions being separated by a first prescribed distance L along said X axis;
   a plurality of guide rails extending parallel to each other along said X axis from said standby position to said photographing position of said carriage means;
   a plurality of guided members mounted on said carriage means, each of said guided members being engageable with and movable along one of said plurality of guide rails; and
   support means mounted on said carriage means for supporting at least one of said guided members, said support means being movable relative to said carriage means by a second prescribed distance S along said X axis, said guided member supported by said support means being moved by a distance equal to L minus S along said guide rail corresponding thereto when said carriage means moves from said standby position to said photographing position.

2. An apparatus according to claim 1, wherein said support means includes a guide plate fixed on said carriage means and extending along said X axis, a slot-shaped guide hole formed in said guide plate and extending along said X axis, a support portion engaged in said guide hole and movable relative to said guide hole along said X axis, and a support plate fixed on said support portion and having said guided member supported by said support means mounted thereon, said support plate and said guide member supported by said support means being reciprocated by said distance S along said X axis when said support portion is moved within said guide hole along said X axis.

3. An apparatus according to claim 2, wherein said support means includes means for biasing said support plate in a biasing direction along said X axis and a stopper positioned at the end of said guide rail disposed in said biasing direction, said guided member being stopped by said stopper and said support portion being moved with respect to said carriage means in a direction opposite said biasing direction when said carriage means is moved in said biasing direction.

4. An apparatus according to claim 3, wherein said biasing means includes a tension spring.

5. An apparatus according to claim 3, wherein said biasing direction is from said photographing position to said standby position.

6. An apparatus according to claim 3, wherein said biasing direction is from said standby position to said photographing position.

7. An apparatus according to claim 2, wherein said support portion includes a shaft fixed on said support plate, a bearing fitted around said shaft and engaged in said guide hole, and a support piece mounted on said shaft and stopped on said guide plate.

8. An apparatus according to claim 2, wherein said support means includes two support portions engaged in said guide hole.

* * * * *